United States Patent [19]

Kull, Jr. et al.

[11] Patent Number: 4,725,609
[45] Date of Patent: Feb. 16, 1988

[54] METHOD OF PROMOTING HEALING

[75] Inventors: Frederick C. Kull, Jr., Durham; Frank A. Voelker, New Hill, both of N.C.

[73] Assignee: Burroughs Wellcome Co., Research Triangle Park, N.C.

[21] Appl. No.: 673,380

[22] Filed: Nov. 20, 1984

[30] Foreign Application Priority Data

Nov. 21, 1983 [GB] United Kingdom ....... 8330969

[51] Int. Cl.$^4$ .............................................. A61K 31/44
[52] U.S. Cl. .................................................... 514/355
[58] Field of Search ........................ 514/343, 350, 355

[56] References Cited

U.S. PATENT DOCUMENTS 4,258,052 3/1981 Yu et al. ............................... 514/350

FOREIGN PATENT DOCUMENTS 0086475 5/1983 European Pat. Off. .
0090892 10/1983 European Pat. Off. .
0100641 2/1984 European Pat. Off. .

OTHER PUBLICATIONS

Infection & Immunity, vol. 28, No. 1, 4/80, pp. 204–211.
Infection & Immunity, vol. 30, No. 2, 11/80, pp. 523–530.
J. of Immunology, vol. 122, No. 5, 5/79, pp. 1785–1790.
J. of Immunology, vol. 125, No. 4, 10/80, pp. 1671–1677.
Chem. Abst., 99, No. 17, 10/83, 137978p.
Chem. Abst., 92 (1960), 47216p.

Primary Examiner—Stanley J. Friedman
Attorney, Agent, or Firm—Donald Brown

[57] ABSTRACT

This invention pertains to the topical use of nicotinamide to promote, angiogenesis, reepithelialization and wound healing. Formulations and vehicles for administering nicotinamide are also within the scope of this invention.

4 Claims, No Drawings

METHOD OF PROMOTING HEALING

The present invention pertains to the topical application of nicotinamide to expedite the healing of wounds of the skin and mucosa (for example, burns, ulcers, blisters, abrasions, lacerations, hemorrhoids, lesions and surgical wounds) and pharmaceutical formulations for this application. As defined herein the term "wound" is to be taken as a disruption of the normal continuity of bodily structure, internal or external, be it caused by physical or other means such as infection or organic dysfunction. (See *Dorland's Illustrated Medical Dictionary*, 25th Ed., p. 1737, W. B. Saunders, Philadelphia (1974).

It is generally believed that the most effective healing takes place naturally, and the role of the physician is to remove obstacles to the normal healing process. This "minimal interference" concept, formulated 200 years ago, is prevalent today (Madden in *Davis-Christopher Textbook of Surgery*, ed. Sabiston, 11th Ed., W. B. Saunders Co. (1977)). Hence, hygene, adequate nutrition (including vitamin mixtures), bandages and anti-infectives are viewed as relieving impediments to healing.

Nicotinic acid (vitamin B3), in combination with other vitamins, nutrients or drugs, has been used systemically to treat wounds. Nicotinamide is the amide of nicotinic acid, and it has been used in man to treat pellegra and a number of diverse diseases, notably schizophrenia, with mixed successes. It is relatively non-toxic, but high quantities (>3 g per day) taken systemically show liver toxicity (Mrochek et al., *Clin. Chem.* 22: 1821, 1976; Winter and Boyer, *N. Engl. J. Med.* 289: 1180, 1973).

We have now discovered that topical application of nicotinamide promotes healing. The healing of epidermal wounds consists of a number of morphologically discernable, synergistic and contiguous events such as inflammation, angiogenesis (blood vessel proliferation), reepithelialization (restoration of the skin), fibroplasia and collagen synthesis. We have found that nicotinamide is an angiogenic factor. We have also found that it enhances the rate of reepithelialization. Thus, in one aspect of the present invention provides a method of enhancement of angiogenesis and reepithelialization in the body of a mammal such as man comprising topical administration to the mammal of a therapeutically effective amount of nicotinamide. This method of treatment greatly reduces the danger of liver damage that could be caused by systemic administration.

While nicotinamide is useful in promoting healing of a variety of skin and mucosa wounds, such as those listed hereinabove, it is especially useful in the treatment of burns. Frequently, in a burn wound the underlying network of blood vessels has been destroyed, and healing is slow because a new network must be established to support the growth of new skin, i.e., reepithelialization. Burns also tend to leave areas of subdermanal tissue exposed to physical insult causing further injury and to infection from microorganisms. In cases where the burned area is extensive, infection is the major complication. By promoting angiogenesis and reepithelialization, and consequently enhanced healing, the period of vulnerability to further injury and infection is reduced significantly.

Another important aspect of this invention is the topical administration of nicotinamide with a variety of other topical therapeutic agents. Such further agents may be administered separately from the nicotinamide, either systemically on topically, or simultaneously. A synergistic advantage is gained by combining nicotinamide with other drugs, drug delivery systems and medical aids intended to provide a favorable environment to natural healing. Such combinations provide rational mixtures of substances which not only minimize impediments, but at the same time, enhance the healing process.

It is convenient to include nicotinamide in a topical pharmaceutical formulation of other drugs and medical aids currently used clinically to provide a favorable environment for healing. Nicotinamide may be used in formulations containing anti-infectives, e.g., an antiviral agent such as acyclovir, idoxviridine or vidarabine or an antibacterial agents such as neomycin, polymyxin B, gentamicin, nystatin, trimethoprim, co-trimoxazole or bacitracin, an analgesic such as benzocaine or an antiinflammatory drug, e.g., corticosteriods such as hydrocortisone, as well as nonsteroidal agents such as pyrazolines. It may also be used with antiparasitic agents including antiprotozoals and agents for countering maggot fly, screw-worm, ticks and mange, e.g., pyrethroids such as permethrin, deltamethrin, cypermethrin, flumethrin or fenvalerate, or parasitic repellants.

Nicotinamide (optionally with one or more other therapeutic ingredients such as those above) can also be impregnated in artificial skin, bandages and dressings. Such impregnated materials constitute a further feature of the present invention.

The amount of nicotinamide required to induce angiogenesis and reepithelialization thus promoting healing will, of course, vary with the condition being treated, and the person undergoing treatment and is ultimately at the discretion of the physician. However, a typical treatment of a wound (as hereinbefore defined) may entail topical administration of nicotinamide at a dosage in the range 1 to 1000 mg per day for a human adult applied at the rate of 0.1 to 10.0 mg/cm$^2$. A dosage of 1 to 3000 mg per day may be used. A typical regime may require the dose to be administered from one to twenty-four applications of nicotinamide per day until angiogenesis has reached a desirable level and/or reepithelialization is complete. It is conceivable that under some conditions a continuous treatment may be required, e.g., in the form of a bath containing nicotinamide. In all cases of topical application, the nicotinamide (preferably in a pharmaceutical formulation as described hereinbelow) is to be brought into direct contact with the wound.

While it is possible for nicotinamide to be administered alone in undiluted form, it is preferable to present it in a pharmaceutical formulation adapted for topical use. Formulations according to the present invention are preferably sterile.

Such a topical formulation may comprise nicotinamide together with one or more pharmaceutically acceptable excipients, diluents and carriers therefor, and optionally one or more other pharmacologically active therapeutic ingredients. The excipient(s), diluents or carrier(s) referred to above must be pharmaceutically acceptable in the sense of being compatible with the other ingredients of the formulation and not deleterious to the recipient thereof. The other therapeutic ingredient(s) may include but are by no means limited to those discussed hereinabove. As used herein, the term 'active ingredient' means nicotinamide alone or in combination with one or more other pharmacologically active ingredients in any desired proportion.

Of the formulations according to the invention, particularly preferred are those formulations adapted for topical application, preferably to the skin or eye. Alternatively, the formulation may be adapted for rectal or buccal (e.g., sub-lingual) administration, or provided that the formulation is within the scope of the invention as hereinbefore defined.

The formulations may take the form of an ointment, cream, suspension, lotion, powder, solution, paste, gel, spray, aerosol or oil. Carriers which may be used include petroleum jelly, lanoline, polyethylene glycols and combinations thereof. The active ingredient is generally present in a composition of from 0.1 to 95% w/w of the composition, for example, preferably 1 to 25%. Methods of preparing topical formulations include the step of bringing the active compound into association with the excipient(s) or carrier(s) which constitute one or more accessory ingredients. In general, the formulations are prepared by uniformly and intimately bringing the active ingredients into association with a finely divided solid, semi-solid or liquid carrier and then packaging in a suitable container. Some applications may require that the formulation be prepared under sterile conditions. The particular form of the topical formulation and the carrier will of course depend on the site of application and the nature of the condition being treated. For some utilities, it is preferably for the formulation to include one or more agents to enhance dermal penetration, e.g., pyrrolidone and its derivatives.

Formulations suitable for rectal administration are preferably presented as unit-dose suppositories. These may be prepared by admixture of the active ingredient with one or more of the conventional solid carriers, for example cocoa butter, and shaping of the resulting mixture.

Formulations adapted for topical use also include dressings such as bandages and adhesive plasters impregnated with active ingredients and optionally one or more excipients or diluents.

The present invention will now be illustrated by the following examples:

EXAMPLE 1

Promotion of Angiogenesis

Angiogenesis was assessed using the corneal micropocket assay in rabbits as described by Fournier, et al., Invest. Ophthalmol. Vis. Sci. 21: 351 (1981). Briefly, 40 μg of nicotinamide were incorporated into 10×1.5 mm³ Elvax (a vinyl polymer) pellets. An unidentified substance isolated from tumor extracts served as the negative control (8 $A_{260\ mm}$ units/pellet). Each pellet was implanted in a cornea 1 mm from the limbus. The number and length of new vessels growing from the limbus to the pellet were determined three times weekly for two weeks. The values in Table I are the average vessel length. The standard error of the mean for each point was approximately 30% of its value. The number in parenthesis indicates the number of implants eliciting any angiogenic response relative to the number evaluated. Inflamed corneas were not included in the tabulation.

TABLE I

| | VESSEL LENGTH (mm) | |
| Day After Implant | Nicotinamide (8/10) | Control (2/6) |
| --- | --- | --- |
| 4 | 0.16 | 0.04 |
| 6 | 0.32 | 0.05 |
| 8 | 0.45 | 0.05 |
| 10 | 0.50 | 0.10 |
| 14 | 0.64 | 0.00 |
| 16 | 0.75 | 0.08 |

EXAMPLE 2

Enhancement of Reepithelialization

Nicotinamide was administered topically twice daily for five consecutive days to make guinea pigs with experimentally—produced burn wounds according to the schedule listed below in TABLE II.

TABLE II

| | TREATMENT SCHEDULE | |
| Group | % Nicotinamide Solutions | Number Animals |
| --- | --- | --- |
| I (control) | 0 | 7 |
| II | 0.01% | 6 |
| III | 0.1% | 7 |
| IV | 1.0% | 7 |

Nicotinamide was dissolved in distilled water with control animals receiving distilled water only.

Hair over the abdomen and thorax was clipped on the day prior to wounding. On the day of wounding the animals were anesthetized with 30 mg/kg sodium pentobarbital administered intraperitoneally and hair over the wound site was removed by shaving. A 1.0 in. (2.54 cm) diameter scald burn wound was made on the dorsolateral aspect of the thorax by immersion in 70° C. water for 10 seconds. A wire gauze shield (with taped edges and a suitably sized aperture to allow access to the wound site for dosing) was taped over the wound to provide protection against abrasion or scratching.

On the day of wounding (Day 1) 0.05 ml drug solution (or distilled water) was applied to the wound site 15 minutes after scalding. The solution was then gently spread out over the surface of the wound using a nonwettable glass rod. Drug solutions were reapplied in a similar manner 6 hours after the first application on Day 1. On Days 2 through five drug solutions were applied twice daily at 6 hour intervals during working hours. Wound sites were evaluated daily during the study for clinically apparent abnormalities such as erythema, swelling or trauma. On the morning of Day 6 the animals were anesthetized by $CO_2$ inhalation and sacrificed by exsanguination. Wound sites and adjacent skin were then excised an placed in Karnovsky's fixative.

Following fixation, wounds were processed, embedded in JB4 plastic embedding medium and sectioned in a microtome. All sections were cut at right angles to the direction of hair growth. Sections were stained with hematoxylin and eosin. A full width of the wound site (2.54 cm) was examined by light microscopy and the percentage of reepithelialization over the wound surfaces were calculated. The wound sites were also evaluated for other histological parameters of healing such as thickness of epithelium, keratinization, etc.

Redness or erythema of skin of the burn areas was noted within 3 to 5 minutes after scalding and this persisted for the duration of the study. Within 5 to 10 minutes after scalding, skin of the burn areas became swollen and there was elevation of the wound margin above peripheral normal areas of skin. The epidermal surface was extremely friable and loosely attached to underlying tissue so that it could be disrupted by slight shearing pressure. Limited regrowth of hair after shaving occurred in the burned area, in contrast to luxuriant regrowth in surrounding nonburned skin.

Histologic examination of burn wounds of the 6th day of the study revealed detachment of the stratum corneum from underlying epithelium so that a blister-like lesion was produced except that fluid distention was absent. There was necrosis of epithelum of the epidermis and of epithelium in the superficial ½ of hair follicles. Epithelial regeneration was evident in varying degrees in wounds of animals from all dose groups. By the end of the study most hair follicle epithelium had regenerated to the level of the original epidermal surface and had begun regenerating over the surface of the dermis beneath the detached original stratum corneum. In addition, a thickened layer of regenerating epithelium was present at the lateral margins of the burn wound indicating healing from the periphery. Focal areas of fibroplasia, vascular proliferation and inflammation cell infiltrates were visible in the dermis in the area of the burn wound. Histopatholigically, there were no differences in type or degree of these latter changes between the control or treated groups of animals.

Significant differences were noted between the control group and treated groups in the extent of reepithelialization of the wound surface. While an average of only 37.2% of the wound surfaces were reepithelialized in the control groups, 73.0%, 65.2% and 86.9% reepithelization was noted in groups treated with 0.01%, 0.1% and 1.0% nicotinamide, respectively (See Table III). Consequently, a significant enhancement of healing was apparent even in the low dose group treated with the lowest level of nicotinamide (0.01%), and reepithelialization of wound surfaces was more than double that of the control group in Group IV treated with the highest concentration (1.0%) of nicotinamide.

Keratinization was present in the superficial aspects of regrowing epithelium, especially in Group IV wounds, and to some extent in burn wounds of Groups II and III. It was not present in regrowing epithelium of the control group (Group I) wounds indicating an earlier or less differented stage of regeneration. There appeared to be no substantial difference in the thickness of regenerating epithelium between dose groups.

TABLE III

Percent Reepithelialization of Burn Wounds Six Days Post-Burn

| Treatment Group | Number of Animals | % Wound Diameter Reepithelialized (Mean) | % Surface Area Reepithelialized (Mean) |
| --- | --- | --- | --- |
| I | 7 | 60.7 ± 11.54 | 37.2 ± 15.64 |
| II | 6 | 85.0 ± 9.02 | 73.0 ± 14.91 |
| III | 7 | 80.1 ± 11.02 | 65.2 ± 18.48 |
| IV | 7 | 93.5 ± 4.43 | 86.9 ± 8.34 |

EXAMPLE 3

Pharmaceutical Formulations

| (A) Ingredients | 1% Anhydrous Ointment Amount per 100 g |
| --- | --- |
| Nicotinamide | 1.0 g |
| Petrolatum, White | q.s. |
| | 100.0 g |

White petrolatum is melted by heating to 45° C.–60° C. Nicotinamide is added and disperse with aid of a mixer. The ointment is then cooled to room temperature.

| (B) Ingredients | 10% Anhydrous Ointment Amount per 100 g |
| --- | --- |
| Nicotinamide | 10.0 g |
| Petrolatum, White | q.s. |
| | 100.0 g |

Preparation as described in (A) above.

| (C) Ingredients | 1% in Water Soluble Ointment Per 100 g |
| --- | --- |
| Nicotinamide | 1.0 g |
| Polyethylene Glycol 400 | 49.5 g |
| Polyethylene Glycol 4000 | 49.5 g |
| | 100.0 g |

The polyethylene glycol 400 and polyethylene glycol 4000 are melted together by heating to 65° C. The nicotinamide is added and dispersed with aid of mixer.

| (D) Example No. Ingredients | 10% in Water Soluble Ointment Per 100 g |
| --- | --- |
| Nicotinamide | 10.0 g |
| Polyethylene Glycol 400 | 45.0 g |
| Polyethylene Glycol 4000 | 45.0 g |
| | 100.0 g |

Preparation as described in (C) above.

| (E) Ingredients | 1% Cream Per 100 g |
| --- | --- |
| Nicotinamide | 1.0 g |
| Petrolatum | 25.0 g |
| Preservative | q.s. |
| Propylene Glycol | 12.0 g |
| Polysorbate 80 | 5.0 g |
| Stearyl Alcohol | 25.0 g |
| Water | q.s. |
| | 100.0 g |

The petrolatum, preservative, propylene glycol, polysorbate 80 and the stearyl alcohol are combined and heated to 70° C. Nicotinamide is dissolved in water at 75° C. and added to the above mixture with vigorous agitation. The mixture is allowed to cool to room temperature while the agitation is continued.

| (F) Ingredients | 10% Cream Per 100 g |
| --- | --- |
| Nicotinamide | 10.0 g |
| Petrolatum | 20.0 g |
| Preservative | q.s. |
| Propylene Glycol | 12.0 g |
| Polysorbate 80 | 5.0 g |
| Stearyl Alcohol | 20.0 g |
| Water | q.s. |

| (F) Ingredients | 10% Cream Per 100 g |
|---|---|
| | 100.0 g |

Preparation as described in (E) above.

| (G) Ingredients | 10% in Water Soluble Ointment with 5% Antiviral Agent (Acyclovir) Per 100 g |
|---|---|
| Nicotinamide | 10.0 g |
| Acyclovir | 5.0 g |
| Polyethylene Glycol 300 | 20.0 g |
| Polyethylene Glycol 4000 | 65.0 g |
| | 100.0 g |

Preparation as described for (C) above.

| (H) Ingredients | 10% in Ointment with Antibacterial Agent (Polymyxin B) Per 100 g |
|---|---|
| Nicotinamide | 10.0 |
| Polymyxin B Sulfate | 110,000 units |
| Petrolatum | 20.0 g |
| Stearyl Alcohol | 20.0 g |
| Polysorbate 80 | 5.0 g |
| Propylene Glycol | 10.0 g |
| Water | q.s. |

Prepared in a similar way to that described for (C) above.

| (I) | 1% Suppository |
|---|---|
| Nicotinamide | 1.00 |
| Hydrogenated Suppository Base | q.s. |
| | 100.00 |

| (J) | 10% Suppository |
|---|---|
| Nicotinamide | 10.00 |
| Hydrogenated Suppository Base | q.s. |
| | 100.00 |

| (K) | 1% Rectal Cream |
|---|---|
| Nicotinamide | 1.00 |
| Cetyl Alcohol | 2.00 |
| Cetyl Esters Wax | 1.00 |
| Glycerin | 5.00 |
| Sodium Lauryl Sulfate | 2.00 |
| Preservatives | q.s. |
| Water | q.s. |
| | 100.00 |

| (L) | 10% Rectal Cream |
|---|---|
| Nicotinamide | 10.00 |
| Cetyl Alcohol | 2.00 |
| Cetyl Esters Wax | 1.00 |
| Glycerin | 5.00 |
| Sodium Lauryl Sulfate | 2.00 |
| Preservatives | q.s. |
| Water | q.s. |
| | 100.00 |

| (M) | 1% Liquid Amount per 100 g |
|---|---|
| Nicotinamide | 1.00 |
| Glycerin | 10.00 |
| Dimethylsulfoxide | 89.00 |
| | 100.00 |

| (N) | 1% Liquid Amount per 100 g |
|---|---|
| Nicotinamide | 1.00 |
| Isopropyl Myristate | 5.00 |
| Dimethylsulfoxide | 94.00 |
| | 100.00 |

| (O) | 10% Liquid Amount per 100 g |
|---|---|
| Nicotinamide | 10.00 |
| Glycerin | 45.00 |
| Dimethylsulfoxide | 45.00 |
| | 100.00 |

| (P) | 10% Liquid Amount per 100 g |
|---|---|
| Nicotinamide | 10.00 |
| Isopropyl Myristate | 5.00 |
| Dimethylsulfoxide | 85.00 |
| | 100.00 |

What we claim is:

1. A method of promoting wound healing comprising the topical application of an effective wound healing amount of nicotinamide to the wounded area of said mammal.

2. A method of enhancing the rate of reepithelialization in a mammal comprising topical application of an effective reepithelialization amount of nicotinamide to that area of said mammal in need of reepithelialization.

3. A method of promoting angiogenesis in a mammal comprising the topical application of an effective angiogenesis amount of nicotinamide to that area of said mammal in need of angiogenesis.

4. A method of claim 1 wherein the wound is a burn.

* * * * *